United States Patent
Wright

Patent Number: 5,172,689
Date of Patent: Dec. 22, 1992

[54] CRYOGENIC SLEEVE FOR PROVIDING THERAPEUTIC COMPRESSION

[76] Inventor: Christopher A. Wright, 171 Bloomingbank Rd., Riverside, Ill. 60546

[21] Appl. No.: 486,782

[22] Filed: Mar. 1, 1990

[51] Int. Cl.⁵ .............................................. A61F 7/00
[52] U.S. Cl. ................................... 128/400; 128/402; 602/2
[58] Field of Search .............. 128/400, 402, 379, 82.1, 128/24.4, 64; 62/259.3; 165/46

[56] References Cited

U.S. PATENT DOCUMENTS

| | | | |
|---|---|---|---|
| 3,871,381 | 3/1975 | Roslonski | 128/400 |
| 3,901,225 | 8/1975 | Sconce | 128/402 |
| 4,338,944 | 7/1982 | Arkans | 128/400 |
| 5,074,285 | 12/1991 | Wright | 128/24.1 |

Primary Examiner—Mark Graham
Attorney, Agent, or Firm—Kinzer, Plyer, Dorn McEachran & Jambor

[57] ABSTRACT

A device for applying cryogenic compression for use in diminishing hemorrhage and edema in acute trauma of body extremities is formed by a sleeve having a plurality of adjacent non-communicating cryogenic chambers and a plurality of coextensive pressure chambers, there being a pressure chamber for each cryogenic chamber. There are fill openings for each cryogenic chamber and inlets for each pressure chamber. A pump is connected to all of the pressure chamber inlets to apply intermittent pressure to one or more of the pressure chambers to thereby apply intermittent cryogenic pressure to an area of a body extremity coextensive with one or more of the cryogenic chambers.

5 Claims, 1 Drawing Sheet

CRYOGENIC SLEEVE FOR PROVIDING THERAPEUTIC COMPRESSION

SUMMARY OF THE INVENTION

The present invention relates to a portable device, specifically a sleeve, for applying intermittent cryogenic compression for the acute care of arm and leg swelling.

A primary purpose of the invention is to provide a sleeve, which may be attached to a body extremity such as an arm or a leg, and which can be utilized to apply compression and cold on an intermittent basis to one or more areas of the body extremity as determined by the plurality of cryogenic chambers formed in the sleeve.

Another purpose of the invention is to provide a device of the type described which may be operable on battery power and thus is portable and may be used at the site of an athletic injury or in transit.

Other purposes will appear in the ensuing specification, drawings and claims.

BRIEF DESCRIPTION OF THE DRAWINGS

The invention is illustrated diagrammatically in the following drawings wherein.

DESCRIPTION OF THE PREFERRED EMBODIMENT

Figures 1, 2:
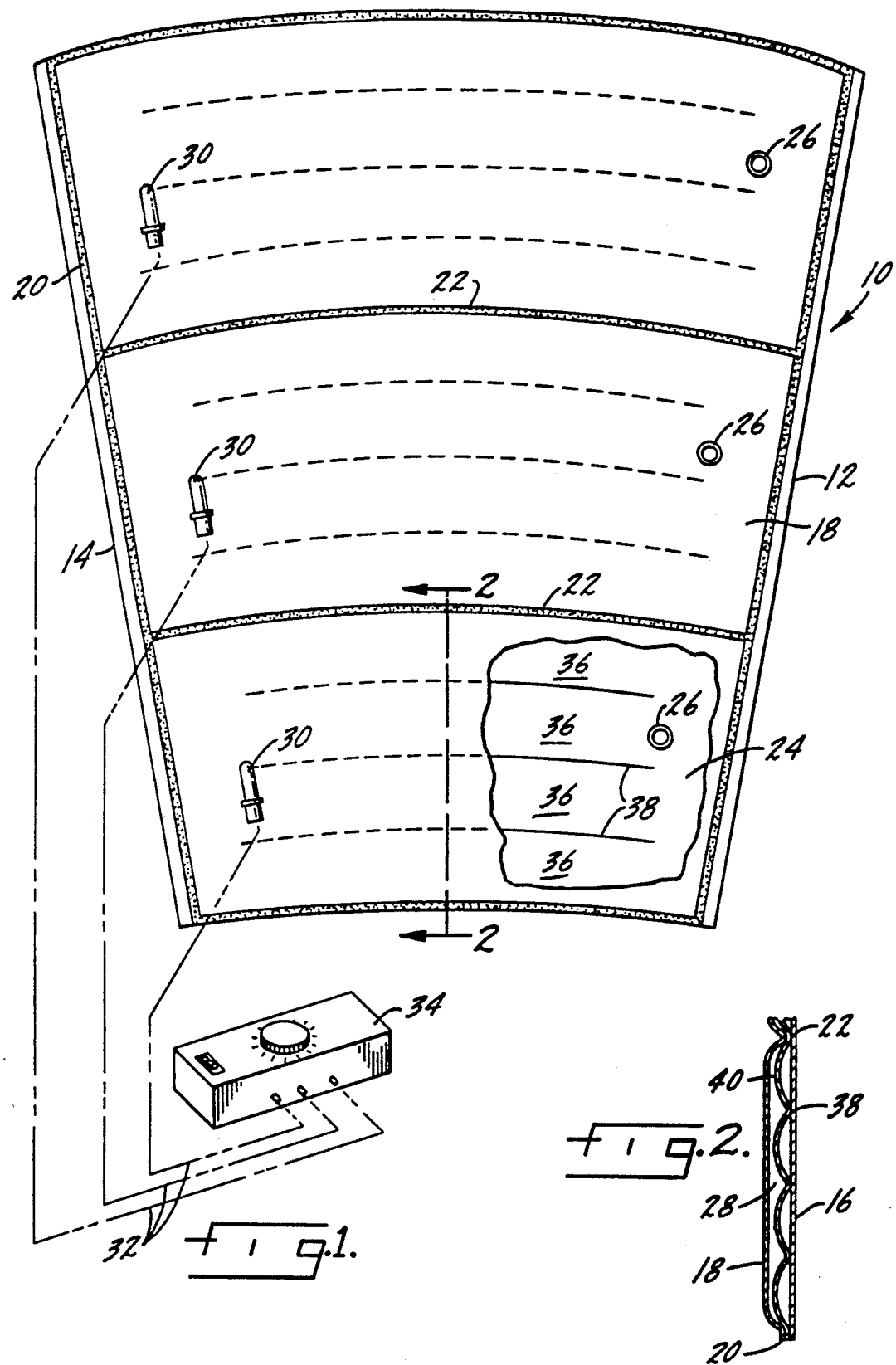
FIG. 1 is a diagrammatic illustration of a cryogenic sleeve of the type described.
FIG. 2 is a section along plane 2—2 of FIG. 1.

For some years cryotherapy has been known to be the treatment of choice in the management of acute athletic injuries. Cryotherapy is effective in diminishing hemorrhage and edema by the combined effect of a decrease in blood flow through damaged capillaries and a reduction in metabolic function at the cell level. Whatever the type of acute trauma (contusion, ligament sprain or complete laceration, muscle strain or complete tear or fracture), ice is the preferred treatment and it should be done immediately. Compression is also known to discourage hemorrhage and edema and is often applied in conjunction with cryogenic therapy. Intermittent compression is a common therapy administered for management of unusual swelling and effusion and intermittent compression is a common, almost mandatory, post surgical therapy as a prophylaxsis to embolism and phlebitis.

U.S. Pat. No. 3,548,819 shows a splint having coextensive chambers, one of which is filled with a therapeutic substance, for example a cryogenic liquid, and the other is filled with air for use in applying both compression and cold to an injured area of the body. U.S. Pat. No. 3,561,435 shows a similar device in which there are separate, although interconnected, cryogenic chambers. U.S. Pat. Nos. 2,781,041 and 4,370,975 both disclose air splints using the application of intermittent and/or sequential pressure for therapeutic purposes, but do not combine such pressure with any kind of cryogenic therapy. Jobst Institute, Inc. of Toledo, Ohio, provides a cryogenic sleeve using the cryogenic chamber to apply compression, which may be intermittent.

The present invention combines cryogenic therapy plus intermittent and/or sequential compression to an injured area of the body. This is brought about in a unique, simply constructed reliable portable sleeve which has a plurality of cryogenic chambers and a plurality of coextensive pressure chambers. A pump is attached to each of the inlets of the pressure chambers and the pump can be programmed to apply sequential or intermittent pressure to one or all of the pressure chambers to thereby apply cryogenic therapy in any desired manner, either sequential or intermittent.

In FIG. 1 the cryogenic therapy sleeve is indicated generally at 10 and is of the type which may be used on a body extremity such as an arm or leg. Opposite longitudinally extending edges 12 and 14 may each include portions of a zipper so that the sleeve, after it surrounds the body extremity, may have its opposite longitudinal sides attached together to provide a complete enclosure of the extremity. Other types of fastening devices may also be used. The sleeve 10 is divided into a plurality, in this case three, although that is only by way of example, coextensive cryogenic chambers and pressure chambers. The cryogenic chambers are on the inside and the pressure chambers are on the outside.

As illustrated specifically FIG. 2, the sleeve includes an inner wall 16 and a coextensive wall 18, both of which may be formed of a suitable fabric having sufficient flexibility for the use described. The inner and outer walls 16 and 18 are peripherally heat sealed or sewn together, as indicated at 20 in FIG. 2. Thus, there is a peripheral seam joining the inner and outer walls. There are a plurality of longitudinally spaced, laterally extending seams 22 which separate the sleeve into the coextensive plurality of chambers. Each of the cryogenic chambers, designated generally at 24, may have a fill opening or fill valve 26 whereby each of the chambers may be individually filled with a cryogenic fluid. The chambers are non-communicating and the filling of one chamber provides no cryogenic fluid for an adjacent chamber. Each of the pressure chambers 28 has an inlet valve 30 so that each of the pressure chambers may be individually activated through lines 32 which connect each of the pressure chambers to a pump 34.

Pump 34 may be operable by conventional 120 volt AC power or it may be operable by a 12 volt battery. The pump may be one of several such devices currently on the market and one such device which is suitable is a pump manufactured by Wright Linear Pump, Inc. of Imperial, Pennsylvania. Such pumps can apply pressure to all cells intermittently or sequentially in any manner desired by the therapist to apply a desired cryogenic therapy. Thus, the chambers may be activated sequentially; all may be activated simultaneously, but intermittently to apply cryogenic compression in a desired manner to diminish hemorrhage and edema in acute trauma of body extremities.

Each of the cryogenic chambers 24 is divided into a plurality of subchambers 36 formed by a plurality of generally parallel, longitudinally spaced and laterally extending intermediate seams or dividers 38 in which an intermediate wall 40, which separates each cryogenic chamber 24 from each pressure chamber 28, is attached to outer wall 16. The seams 38 do not extend the entire lateral extent of each pressure chamber, but stop short of each of the side walls. Each of the subchambers is thus interconnected by the open areas at the sides. The principal purpose of the subchambers is to insure that there is a generally uniform distribution of the cryogenic substance over the entire area of each chamber 24.

In use, the sleeve 10 will be placed adjacent an injured portion of a body extremity and the opposite edges 12 and 14 will be joined together by the zipper on the sleeve edges. In the alternative, other forms of fastening may be used. The cryogenic chambers are filled by a suitable substance through inlet valves 26. Pump 34 will be connected to each of the pressure inlets 30. The pump will be set so as to apply pressure in a desired sequence for the particular desired therapy. The pressure may be sequential and/or intermittent, depending upon the nature of the injury and the duration of the therapy. What is important is that the sleeve 10 is subdivided into individual chambers, each of which has a coextensive pressure chamber so that defined areas of the injured extremity may have cryogenic compression and in any desired manner. By limiting the size of each cryogenic chamber, it is possible to apply cryogenic compression to a very limited area of a body extremity, and by having a plurality of such chambers it is possible to have intermittent and/or sequential application of cryogenic compression.

Whereas the preferred form of the invention has been shown and described herein, it should be realized that there may be many modifications, substitutions and alterations thereto.

The embodiments of the invention in which an exclusive property or privilege is claimed as defined as follows:

1. A cryogenic device for use in diminishing hemorrhage and edema in acute trauma of body extremities includes a sleeve with longitudinal extending sides having a plurality of adjacent non-communicating cryogenic chambers, a fill opening for each cryogenic chamber, a plurality of pressure chambers, with each pressure chamber having an inlet and being generally coextensive with and exterior of a cryogenic chamber, said sleeve cryogenic chambers and coextensive pressure chambers being formed by a sleeve inner wall and a coextensive sleeve outer wall, each of which extends over the entire area of the sleeve, said sleeve inner and outer walls being peripherally joined, intermediate wall means separating each cryogenic chamber from its coextensive pressure chamber, said inner and outer walls and intermediate wall means being joined along longitudinal spaced laterally extending seams to form said plurality of coextensive cryogenic and pressure chambers, a pump connected to all of said pressure chamber inlets and formed and adapted to apply pressure intermittently to one or more of said pressure chambers to thereby apply intermittent cryogenic pressure to an area of a body extremity coextensive with one or more of said cryogenic chambers.

2. The cryogenic device of claim 1 wherein each of said cryogenic chambers includes a plurality of dividers separating each cryogenic chamber into a plurality of communicating subchambers.

3. The cryogenic device of claim 1 wherein said intermediate wall means is sealingly attached along a plurality of longitudinally spaced laterally extending locations to form a plurality of communicating subchambers within each crygoenic chamber.

4. The cryogenic device of claim 3 further wherein each of said subchambers terminates short of the longitudinally extending sides of said sleeve.

5. The cryogenic device of claim 1 fastening means for use in connecting opposite longitudinal edges of said sleeve.

* * * * *